(12) United States Patent
Dobert et al.

(10) Patent No.: US 6,570,953 B1
(45) Date of Patent: May 27, 2003

(54) METHOD FOR MAKING AND REPRODUCING A TOMOGRAM OF AN OBJECT, SAID TOMOGRAM PERTAINING TO A SECTION ROENTGENOGRAM

(75) Inventors: Michael Dobert, Lorsch (DE); Roland Bonk, Stutensee (DE)

(73) Assignee: Airona Dental Systems GmbH, Bensheim (DE)

( * ) Notice: Subject to any disclaimer, the term of this patent is extended or adjusted under 35 U.S.C. 154(b) by 0 days.

(21) Appl. No.: 09/937,256

(22) PCT Filed: Mar. 22, 2000

(86) PCT No.: PCT/DE00/00867

§ 371 (c)(1),
(2), (4) Date: Feb. 5, 2002

(87) PCT Pub. No.: WO00/56217

PCT Pub. Date: Sep. 28, 2000

(30) Foreign Application Priority Data

Mar. 22, 1999 (DE) .......................................... 199 12 854

(51) Int. Cl.$^7$ ............................... A61B 6/00; A61B 6/14
(52) U.S. Cl. ............................... 378/21; 378/4; 378/38; 378/58; 378/207
(58) Field of Search ................ 378/4, 21, 38, 378/58, 207, 901; 382/131

(56) References Cited

U.S. PATENT DOCUMENTS

| | | | | |
|---|---|---|---|---|
| 4,196,351 A | * | 4/1980 | Albert | ....................... 378/98.6 |
| 4,878,234 A | | 10/1989 | Pfeiffer et al. | ................. 378/40 |
| 5,287,276 A | * | 2/1994 | Crawford et al. | .............. 378/4 |
| 5,668,844 A | * | 9/1997 | Webber | ......................... 378/2 |
| 5,784,429 A | * | 7/1998 | Arai | ............................. 378/38 |
| 5,828,722 A | | 10/1998 | Ploetz et al. | .................. 378/38 |
| 6,049,584 A | | 4/2000 | Pfeiffer | ......................... 378/39 |
| 6,459,760 B1 | * | 10/2002 | D'Ambrosio | ................ 378/43 |

FOREIGN PATENT DOCUMENTS

EP 0 000 079 6/1978

* cited by examiner

*Primary Examiner*—Drew A. Dunn
*Assistant Examiner*—Allen C. Ho
(74) *Attorney, Agent, or Firm*—Schiff Hardin & Waite

(57) ABSTRACT

In a method and x-ray apparatus for making and reproducing a radiological tomogram of a subject, the subject is irradiated with radiation emanating from a focus disposed at a known distance from a focal plane, situated at the subject. The focal plane is disposed at a known distance from a radiation receiver, which is disposed in the image plane, and which contains a number of picture elements. In a digital radiological tomogram, either the slice position with the aforementioned distances is allocated to respective picture elements, or a correction factor, based on the slice position and the aforementioned distances, is allocated to the respective picture elements, from which a corrected image is obtained with the subject appearing with a corrected size corresponding to the size of the subject in the focal plane.

17 Claims, 3 Drawing Sheets

METHOD FOR MAKING AND REPRODUCING A TOMOGRAM OF AN OBJECT, SAID TOMOGRAM PERTAINING TO A SECTION ROENTGENOGRAM

BACKGROUND OF THE INVENTION

1. Field of the Invention

The invention is directed to a method for the production and playback of a topographic image of a subject from a radiological tomogram, particularly in the imaging of X-rays on a digital pickup system for the generation of tomograms, particularly panorama tomograms.

2. Description of the Prior Art

In X-ray exposures, in digital X-ray exposures as well, the beam path—proceeding from a radiation source, the focus—passes through the transirradiated subject wherein the focal plane lies, for example the upper or lower jaw regions, before the rays impinge the sensor plane wherein the subject is imaged. The respective distances between the focal plane and the focus, and between the focal plane and the sensor or reception plane, usually are derived from the dimensions of the subject to be transirradiated and from the pickup conditions.

The beam path from the radiation source through the focal plane into the plane receiving the radiation follows the laws of the radiation theorem. Emanating from the radiation source, the ray beam proceeds through the focal plane that is located in the subject to be imaged. The subject has its true size, in the scale of 1:1, in the focal plane. Proceeding from the subject plane, the ray beam continues to expand—now influenced in intensity and contrast by the subject—and as a result the subject of the focal plane is enlarged in the vertical and horizontal directions dependent on the distance of the focal plane from the sensor or reception plane and, thus, is distorted. The subject, for example individual teeth or entire sections of the upper or lower jaw, are imaged enlarged in the reception plane by a factor that lies between 1.05 and 1.24 as viewed in the vertical direction. Without correction, a distorted presentation of the subject on the imaging plane arises in X-ray exposures, even in digital X-ray exposures.

The vertical and horizontal distortion of individual regions of the X-ray image must be taken into consideration in the diagnosis of such an X-ray image and the interpretation of special characteristics based on the X-ray image. The distorted regions of the X-ray image must be visually interpolated in order to achieve true-to-scale conditions on the X-ray image. This can lead to errors in the interpretation, particularly arising from the spatial allocation that is frequently difficult to estimate.

Heretofore, the above factors have been addressed by determining the actual size conditions of the region to be diagnosed from the film or from the printout given digital X-ray exposures with the assistance of back-calculations, templates or from the radiation theorem given a known magnification factor between the subject and the reception plane.

German OS 196 19 925 discloses that the position and spatial orientation of the examination subject and the changes thereof during the implementation of the exposure given panorama X-ray devices for producing tomograms be acquired by measurement with a position detector. Correction signals are then formed from the signals of the position detector in order to allocate the correct image contents to the subject details from the desired slice to be sharply imaged before the implementation of the tomographic blurring effect and to follow up the position of the desired slice with respect to the patient movement. This size correction only serves to assist in the interpretation of the image contents acquired in the individual frames with topical precision for generating a tomosynthetic image reconstruction. The complicated method of tomosynthetic image reconstruction, however, is not required for the production of panorama tomograms.

SUMMARY OF THE INVENTION

In accordance with the present invention, in a method and x-ray apparatus for making and reproducing a radiological tomogram of a subject, the subject is irradiated with radiation emanating from a focus disposed at a known distance from a focal plane, situated at the subject. The focal plane is disposed at a known distance from a radiation receiver, which is disposed in the image plane, and which contains a number of picture elements. In a digital radiological tomogram, either the slice position with the aforementioned distances is allocated to respective picture elements, or a correction factor, based on the slice position and the aforementioned distances, is allocated to the respective picture elements, from which a corrected image is obtained with the subject appearing with a corrected size corresponding to the size of the subject in the focal plane.

The inventive method has a number of advantages. The diagnostic content of digital X-ray exposures can be considerably improved with the method since geometrical conditions can be matched to one another better and uncertainty factors that occur given back-calculations and due to estimating are precluded. By means of the correction of the magnification factor to, for example, the true-to-scale size of 1:1 prevailing in the subject plane, an additive overall image can be produced in a number of slice positions and be played back on the picture screen in many types of presentation.

In a further embodiment of the inventive method, a digital imaging in the image plane can be registered with a sensor having pixels generating picture elements arranged in rows and columns. The buildup of the digital imaging ensues by column-by-column readout of the pixels from the sensor during the rotation of a focus around a center. During the rotation of the focus around the center along the focal curve, the coordinates of a defined slice position are allocated to the picture elements of the registered subject. This allocation of the subject and the slice position to the correction values, and or the correction values themselves, are preferably stored; so that this information can then be accessed again.

A correction of the magnification factor then ensues such that each picture element for a prescribed slice position is recalculated in height relative to the height that is present in the focal plane, i.e., for example, of the upper or lower jaw to be imaged.

In a further embodiment of the invention, the picture elements can also be recalculated in width for each prescribed slice position.

The picture elements recalculated relative to the height of the subject plane, i.e. of the focal plane, can then be imaged in the image plane corrected in this way, and, for example, can be visually presented true-to-scale without distortion in the scale 1:1 on a monitor of a picture screen. This true-to-scale imaging without distortion obtained by recalculation of the picture elements can subsequently be further-processed in many ways.

Advantageously, an overall image is calculated from all recalculated slice positions, this overall image, in particular, being able to be implemented such that the subject is imaged in the corrected exposure in the same size which it has in the focal plane.

The method is especially advantageous when picture elements having different spacings are generated and/or present in a slice position of the radiological tomogram, so that different depths of field can be produced within a slice position and the different imaging scales can thereby be taken into consideration. The fundamental principle for producing tomograms with different depth information or, respectively, depth of field is disclosed by German OS 197 33 338 which corresponds to U.S. Pat. No. 6,049,584, the teachings of which are incorporated herein by reference.

The inventive correction method can be especially advantageously employed in an X-ray device for registering digital X-ray exposures, wherein a focus is movable along a focal curve around a center, a sensor lies in the image plane, and the image size of the picture elements lying in the image plane for prescribed slice positions is converted onto a corrected image size of the subjects in the focal curve, for which purpose means are provided wherein the correction factors belonging to the picture elements of a slice position are stored. As a result, it is possible to implement the inventive correction dependent on the slice position.

Again with reference to German OS 197 33 338, an X-ray apparatus is designed such that, for subsequent determination of the sharp slice and/or of the depth of field, the sensor is composed of a number of narrow zones that can be read out, to generate tomographic image information with high depth of field and predetermined slice position. This image information is individually read out and calculated for an image of slight depth of field in an image processing unit, whereby the distance of this image from the focal plane can be determined by varying the topical offset of the individual tomographic images with the assistance of an input device that influences the image processing.

DESCRIPTION OF THE PREFERRED EMBODIMENTS

Figure 1:
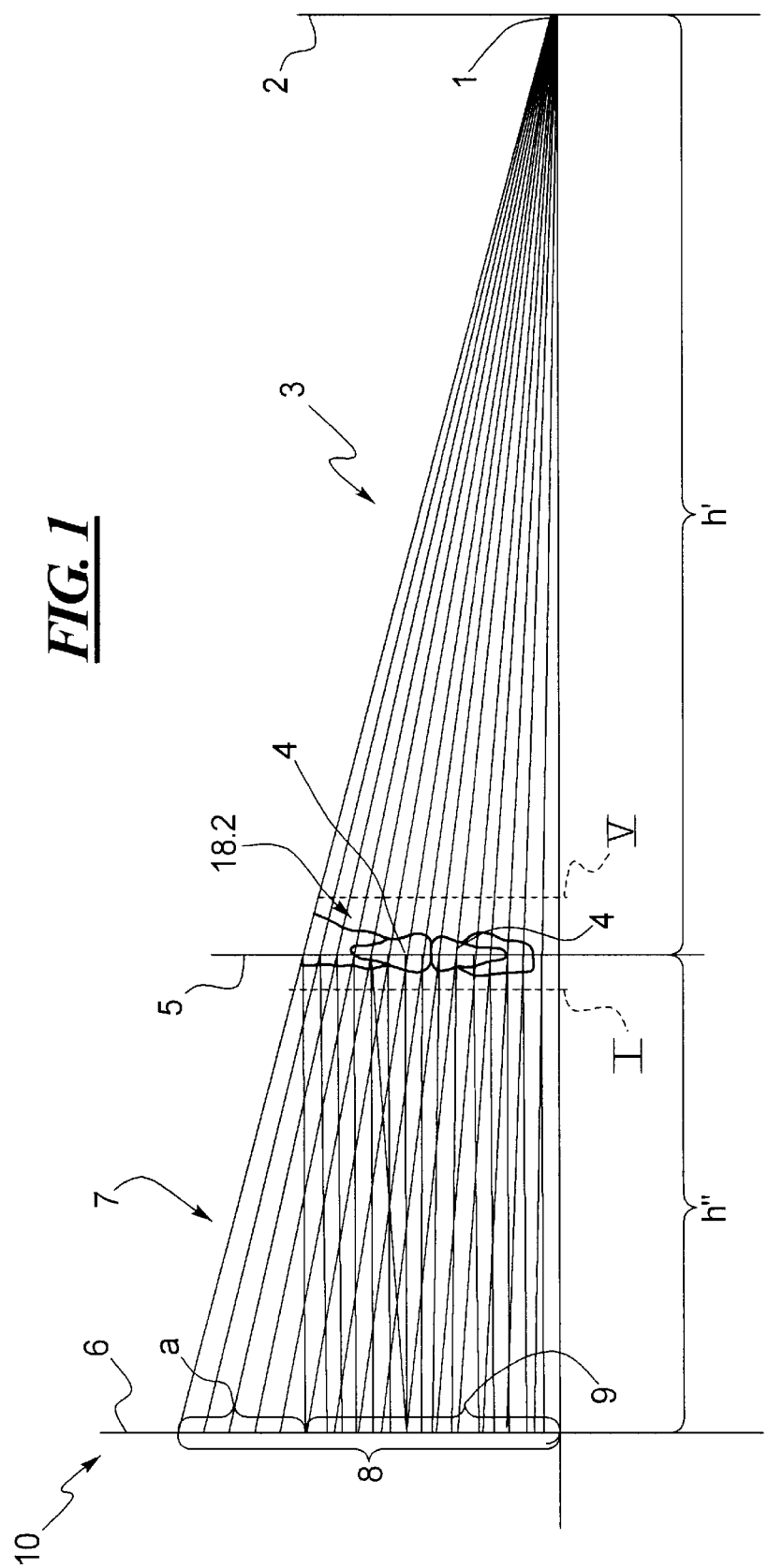
FIG. 1 illustrates the beam path from the focus through the focal plane onto a sensor plane, in the method and apparatus of the invention.

FIG. 1 shows the beam path proceeding from the focus through the focal plane onto a sensor plane.

It proceeds from the schematic sketch that a focus 1, for example an X-ray source 2, emits an X-ray beam 3. As shown in FIG. 1, the ray beam fans out and penetrates a subject 4 in a focal plane 5 that is located at the known distance h' from the focus 1. In the present case according to FIG. 1, the teeth of the upper and lower jaw lie in the focal plane 5, these being penetrated by the ray beam 3.

The focal plane 5 can come to lie between the positions I and V with modified distances h' and h" when the same subject is repeatedly transirradiated or other measures are undertaken in order to influence the depth of field, as disclosed, for example, in U.S. Pat. No. 6,049,584, but can also be caused by multiple exposures.

The ray beam 7 influenced by absorption is incident in the reception of image plane 6 onto a sensor 10 arranged thereat.

According to the radiation theorem, the subjects of the focal plane 5, instead of being imaged in their true-to-scale (M 1:1) size 9, are imaged with the height h in the image plane 6 with a magnification factor that is between 1.05 and 1.24 given dental panorama tomograms.

The radiation-sensitive surface (image plane 6) of the sensor 10 is arranged at a known distance of h" from the focal plane 5. The distortion of the image in vertical direction is references 'a', this causing the vertical extent of the image to appear not-to-scale.

The sensor 10 arranged in the image plane 6 comprises radiation-sensitive pixels on its surface. The pixels are respectively arranged symmetrically distributed relative to the middle of the radiation-sensitive area. The radiation-sensitive surface of the sensor can comprise 66 (or more) columns extending in vertical direction, each thereof being in turn capable of being subdivided into 1500 (or more) rows. A pixel can thereby be allocated to exactly one row and one column, as a result whereof each pixel on the surface of the sensor can be unambiguously addressed.

Per TDI pulse with which the X-ray exposure is made, a complete pixel column is read out per signal output from the sensor 10 functioning, for example, as shift register, whereas the column lying closest in pickup direction is thereby simultaneously re-exposed again; the X-ray exposure thus arises by columns, whereas the slice position for which the registered, column-by-column pixel column was just read out is simultaneously identified and stored. An allocation between pixel column and appertaining slice position—for example, in the upper or lower jaw—is thus assured (see FIG. 2a).

Figure 2A:
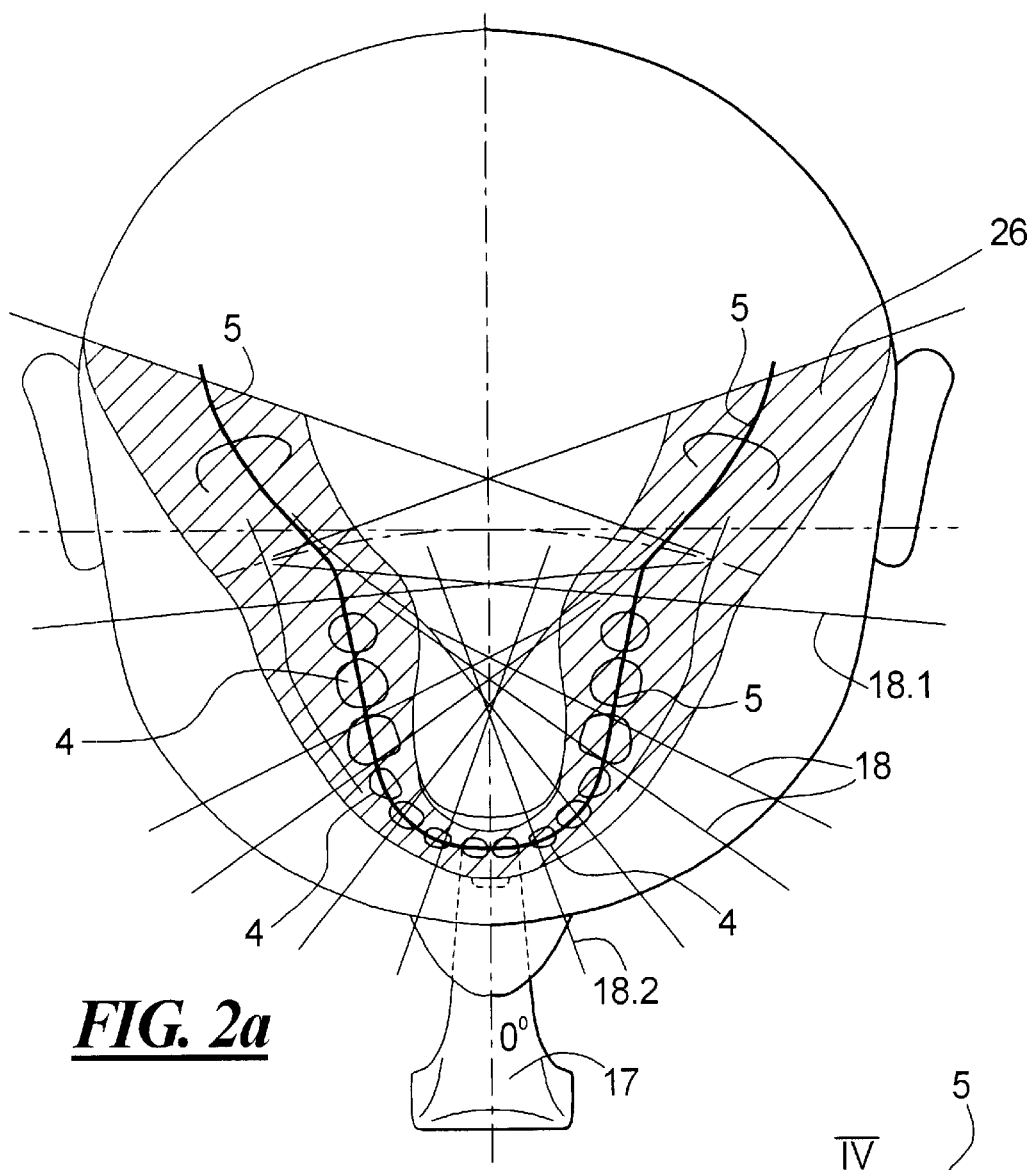
FIG. 2a shows a complete slice position exposure in accordance with the invention.

FIG. 2a shows a complete slice position exposure with stylized indication of the sharply imaged jaw region, referenced as slice thickness curve 26.

The entire transirradiated jaw containing the focal plane 5 is traversed during the pickup cycle of the X-ray exposure, i.e. during the revolution of the focus 1 around a pivot point, and each slice position indicated here by strokes 18 is imaged. 18.1 references a slice position that lies in the molar region wherein the jaw is somewhat thicker. Compared to the slice position 18.1, the slice position 18.2 penetrating the incisor region at the upper and lower jaw is considerably thinner. The slice positions 18 respectively encompass the focal plane 5 and represent the regions wherein the subjects 4 are sharply imaged. The slice position thickness can be thicker or thinner dependent on the jaw anatomy but is known in the production of the X-ray exposure.

Last but not least, the thickness of the slice position is related to the size of the distance h" between the focal plane 5 and the sensor. Due to the jaw anatomy, the distance h' between focus 1 and the subject 4 lying in the focal plane 5 changes during the pickup of the X-ray image. As a result, the distance h" between subject 4 and the image reception plane 6 also changes during the pickup of the X-ray image. The distance h" is slight in the molar region but considerably larger in the region of the front teeth.

Figure 2B:
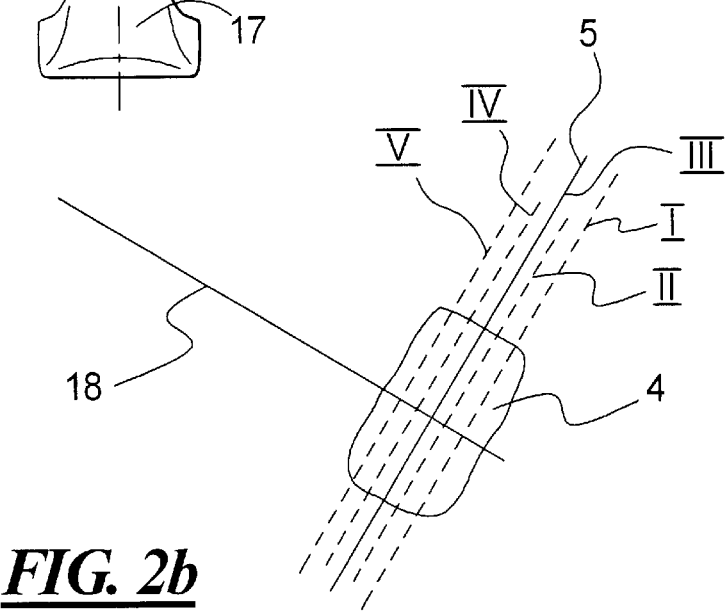
FIG. 2b is a detailed view with the sharp slice along the focal plane, in accordance with the invention.

FIG. 2b shows various sharp slices I through V through the subject 4 that respectively correspond to the focal plane 5 with corresponding offset in the direction of the slice position 18. Depth information are acquired as a result that are respectively corrected in size upon transition from one sharp slice I to the next sharp slice II, etc., so that a comparison tomographic image of the same size is always present of the subject 4 with a respectively different sharp slice despite the beam widening.

In order to assure a defined position of the upper jaw and lower jaw relative to one another and to the focus 5 and the sensor 10 during the buildup of the X-ray exposure that enhances the diagnostic force of the X-ray image, a bite-down means 17 is shown that aligns upper and lower jaw of the patient relative to one another.

Figure 3:
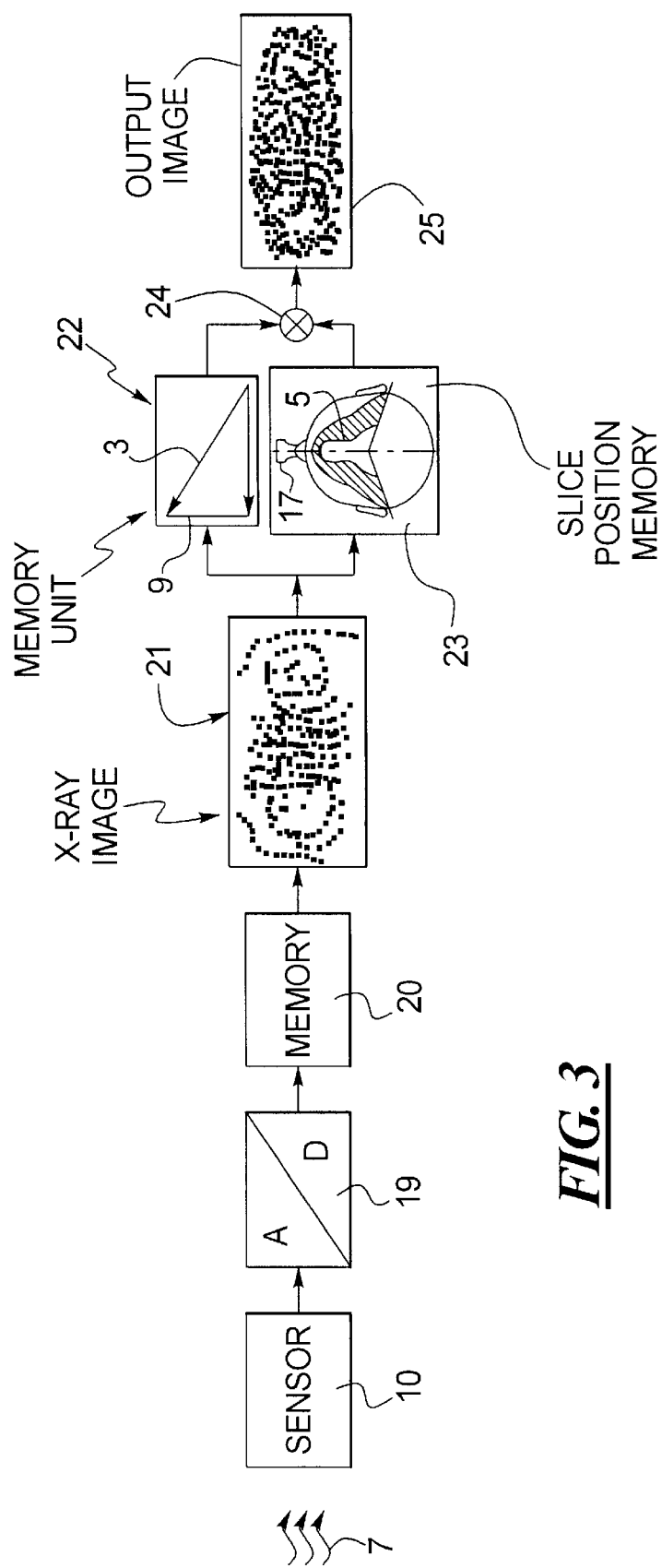
FIG. 3 is a block diagram of an arrangement in accordance with the invention for correcting the enlargement factor.

FIG. 3 shows an evaluation sequence that serves for the correction of the magnification factor in the X-ray image.

After penetrating the subjects lying in the focal plane 5, the ray beam 3, 7 impinges the pixels of the sensor, which supplies the image data that are obtained to an A/D converter 19 column-by-column for digitalization. In the A/D converter 19, the image data that are present in analog form are digitalized for each illuminated pixel and are supplied to a memory 20. The overall X-ray image 21, which is exaggerated by a subject magnification factor between 1.05:1 and 1.24:1, is constructed from the image data that are obtained per revolution and arise column-by-column.

Since every pixel/picture element is addressable with its coordinates x, y in a memory unit 22, the height 9 of the pixel can be preselected for the subject plane with the appertaining magnification factors, which are known from the distances h', h", so that the outside pixel does not assume its stretched height 8 in the reception plane 6, but computationally assumes the true-to-scale height 9.

All transirradiated slice positions 18 are stored in a slice position memory 23 during the X-ray exposure, and these can now be linked with the corrected heights 9 of the pixels, for example by pixel columns. An image 25 that can be output in subject size in the scale 1:1 can be constructed from the linking of the corrected pixel height 9 with the respective slice position 18. A reconstruction of the digitalized X-ray exposure ensues in the calculating unit 24, whereby different magnification factors along the focal plane can also be taken into consideration as a result of the determination of the pixel height 9 for each pixel column. All slice positions 18 converted onto the scale of 1:1 can be added to form an overall image and can also be subtracted therefrom as needed.

In addition to the conversion of the slice positions 18 to the scale 1:1, these can also be converted into arbitrary other scales. The image information present by columns in the evaluation unit 24 according to FIG. 3 can definitely be corrected such with the appertaining magnification factors that both an X-ray exposure in the scale 1:1 as well as an X-ray exposure 25 intentionally distorted in width and/or height arises.

The converted layers 18 can be displayed on a monitor in many ways; an output on a printer or on some other medium is also conceivable.

In addition to the application of the inventive method to digital exposures that can be acquired with sensors, the focal parameters can also be allocated to the digitalized image according to the applied purpose and edited given film exposures that were converted into digital form.

Although modifications and changes may be suggested by those skilled in the art, it is the intention of the inventor to embody within the patent warranted hereon all changes and modifications as reasonably and properly come within the scope of his contribution to the art.

What is claimed is:

1. A method for production and playback of a tomographic image of a subject from a radiological tomogram produced by irradiating a subject with radiation from a focus disposed at a known distance (h') from a focal plan at said subject, with said focal plane being disposed at a known distance (h") from a radiation receiver disposed in an image plane, so that a slice position is irradiated, said radiological tomogram being comprised of a plurality of picture elements, said method comprising the steps of:

obtaining a digital radiological tomogram as said radiological tomogram;

defining a correction region in said radiological tomogram comprising a plurality of said picture elements;

producing an allocation of the slice position with said distances (h'; h") to the picture elements of said subject;

converting each picture element of said image plane into a converted picture element dependent on said allocation; and producing a correction exposure with each converted picture element from said image plane disposed therein dependent on said allocation.

2. A method as claimed in claim 1 wherein the step of obtaining a digital radiological tomogram comprises directly producing a digital radiological tomogram from said subject.

3. A method as claimed in claim 1 wherein the step of obtaining a digital radiological tomogram comprises fetching a digital radiological tomogram from a memory.

4. A method as claimed in claim 1 wherein the step of obtaining a digital radiological tomogram comprises producing an analog radiological tomogram directly from said subject, and digitalizing said analog radiological tomogram to produce a digital radiological tomogram.

5. A method as claimed in claim 1 wherein the step of producing an allocation of said slice position with said distances (h'; h") to the picture elements of the subject comprises allocating respective correction factors to said picture elements in a correction region dependent on said slice position and said distances (h'; h"), and wherein the step of converting said picture elements of said imaging plane comprises converting said picture elements of said image plane in said correction region using said correction factors.

6. A method as claimed in claim 5 comprising registering an image in said image plane with a sensor having pixels that representing said picture elements arranged in rows and columns, by building up said image with column-by-column readout of said pixels from said sensor during rotation of said focus around a center, and allocating coordinates in said focal plane of said slice position to picture elements of said subject during rotation of said focus.

7. A method as claimed in claim 1 comprising registering an image in said image plane with a sensor having pixels that representing said picture elements arranged in rows and columns, by building up said image with column-by-column readout of said pixels from said sensor during rotation of said focus around a center, and allocating coordinates in said focal plane of said correction values to picture elements of said subject during rotation of said focus.

8. A method as claimed in claim 1 comprising converting a height of each picture element for a predetermined slice position into a height of that picture element in said focal plane to produce said converted picture elements.

9. A method as claimed in claim 8 comprising converting every picture element in said image plane into respective converted picture elements.

10. A method as claimed in claim 1 comprising converting a width of each picture element for a predetermined slice position into a width of that picture element in said focal plane to produce said converted picture elements.

11. A method as claimed in claim 10 comprising converting every picture element in said image plane into respective converted picture elements.

12. A method as claimed in claim 1 comprising producing a visible image from the converted picture elements in said correction exposure.

13. A method as claimed in claim 1 comprising producing an overall image of said subject from a plurality of correction exposures respectively obtained from a plurality of slice positions.

14. A method as claimed in claim 1 comprising imaging said subject in said corrected exposure with a same size that said subject has in said focal plane.

15. A method as claimed in claim 1 wherein picture elements having respectively different distances (h'; h") exist in said slice position of said radiological tomogram.

16. An x-ray apparatus comprising:

A radiation source having a focus, said radiation source emitting radiation from said focus and being adapted to irradiate a focal plane in an examination subject, said focal plane being disposed at a known distance (h') from said focus;

A radiation detector disposed at a known distance (h") from said focal plane, on which radiation attenuated by said examination subject is incident;

A memory containing correction values for respective picture elements of a slice position of said subject; and A processor having access to said memory for correcting an image size of respective picture elements in an image plane for respective slice positions using said correction values, to produce a corrected image wherein said subject is shown with a correct image size in said focal plane.

17. An x-ray apparatus as claimed in claim 16 wherein said detector comprises a plurality of narrow zones, and has a read-out arrangement for reading tomographic image information successively from said zones with a high depth of field for a predetermined slice position, and wherein the read-out image information are converted for producing an image with a low depth of shield in said processor, said distances (h'; h") of said image with a low depth of field being identified by modifying a spacial offset of said individual tomographic images with an input device.

* * * * *

UNITED STATES PATENT AND TRADEMARK OFFICE
CERTIFICATE OF CORRECTION

PATENT NO. : 6,570,953 B1
DATED : May 27, 2003
INVENTOR(S) : Michael Dobert et al.

It is certified that error appears in the above-identified patent and that said Letters Patent is hereby corrected as shown below:

<u>Title page,</u>
Item [73], Assignee, change "Airona Dental Systems GmbH" to
-- Sirona Dental Systems GmbH --

Signed and Sealed this

Twentieth Day of January, 2004

JON W. DUDAS
*Acting Director of the United States Patent and Trademark Office*